United States Patent
Barthold et al.

(10) Patent No.: US 9,861,503 B2
(45) Date of Patent: Jan. 9, 2018

(54) STENT GRAFT WITH FIXING ELEMENTS AND INSERTION SYSTEM

(71) Applicant: JOTEC GmbH, Hechingen (DE)

(72) Inventors: Franz-Peter Barthold, Balingen (DE); Marcos Centola, São Paulo (BR); Christian Woerne, Ostifildern (DE)

(73) Assignee: JOTEC GmbH, Hechingen (DE)

( * ) Notice: Subject to any disclaimer, the term of this patent is extended or adjusted under 35 U.S.C. 154(b) by 0 days.

(21) Appl. No.: 14/445,795

(22) Filed: Jul. 29, 2014

(65) Prior Publication Data

US 2014/0336745 A1 Nov. 13, 2014

Related U.S. Application Data

(63) Continuation of application No. PCT/EP2013/052584, filed on Feb. 8, 2013.

(30) Foreign Application Priority Data

Feb. 10, 2012 (DE) .......................... 10 2012 101 103

(51) Int. Cl.
*A61F 2/07* (2013.01)
*A61F 2/82* (2013.01)
(Continued)

(52) U.S. Cl.
CPC .................. *A61F 2/82* (2013.01); *A61F 2/07* (2013.01); *A61F 2/95* (2013.01); *A61F 2/915* (2013.01);
(Continued)

(58) Field of Classification Search
CPC ...... A61F 2002/9505; A61F 2002/9511; A61F 2/07
See application file for complete search history.

(56) References Cited

U.S. PATENT DOCUMENTS

| 5,776,186 A | 7/1998 | Uflacker |
| 5,843,162 A * | 12/1998 | Inoue ........................ A61F 2/07 |
| | | 606/194 |

(Continued)

FOREIGN PATENT DOCUMENTS

| DE | 10335948 | 2/2005 |
| EP | 1117341 | 12/2004 |

(Continued)

OTHER PUBLICATIONS

Mailed Sep. 18, 2014—English Translation of the International Preliminary Report on Patentability (Chapter 1).

(Continued)

*Primary Examiner* — Diane Yabut
(74) *Attorney, Agent, or Firm* — Casimir Jones, SC

(57) ABSTRACT

The present invention relates to a stent graft and to an insertion system for the stent graft according to the invention. The stent graft includes a stent graft portion with a self-expanding stent having successive rings of meandering supports and a first prosthesis material secured on the rings. On at least one of its rings, the stent graft portion has two loop-shaped fixing elements which are attached via a common fixing area and which are attached to the supports of the rings in such a way that, due to the fact that they are guided in opposite directions around the hollow cylindrical body, the latter is compressible. Furthermore, the insertion system according to the invention also has a pin element with which the loop-shaped fixing elements can be threaded on.

8 Claims, 3 Drawing Sheets

(51) Int. Cl.
*A61F 2/95* (2013.01)
*A61F 2/915* (2013.01)

(52) U.S. Cl.
CPC . *A61F 2002/075* (2013.01); *A61F 2002/9505* (2013.01); *A61F 2002/9511* (2013.01); *F04C 2270/041* (2013.01)

(56) References Cited

U.S. PATENT DOCUMENTS

| | | | |
|---|---|---|---|
| 5,873,906 A | 2/1999 | Lau | |
| 8,100,958 B2 | 1/2012 | Fischer | |
| 2004/0138734 A1* | 7/2004 | Chobotov et al. | 623/1.11 |
| 2006/0095119 A1 | 5/2006 | Bolduc | |
| 2007/0043425 A1* | 2/2007 | Hartley et al. | 623/1.12 |
| 2007/0100427 A1 | 5/2007 | Perouse | |
| 2012/0158121 A1* | 6/2012 | Ivancev et al. | 623/1.13 |

FOREIGN PATENT DOCUMENTS

| | | |
|---|---|---|
| EP | 1964532 | 12/2010 |
| JP | 2005-245985 A | 9/2005 |
| JP | 2007-508067 A | 5/2007 |
| JP | 2009-512498 | 3/2009 |
| JP | 4778436 B | 8/2011 |
| WO | 02/083038 | 10/2002 |
| WO | 2005/034808 | 4/2005 |
| WO | 2005/037076 | 4/2005 |
| WO | 2007/053233 A2 | 5/2007 |
| WO | 2011/063972 | 6/2011 |

OTHER PUBLICATIONS

Examination Report (and English translation) dated Sep. 1, 2015 from related JP Patent Application No. 2014-556078.
Notification of Reasons of Refusal, JP Patent Application No. 2014-556078, dated Oct. 3, 2017.

* cited by examiner

STENT GRAFT WITH FIXING ELEMENTS AND INSERTION SYSTEM

CROSS-REFERENCES TO RELATED APPLICATIONS

This application is a continuation of international patent application PCT/EP2013/052584, filed on Feb. 8, 2013, designating the U.S., which international patent application has been published in German language and claims priority from German patent application DE 10 2012 101 103.6, filed on Feb. 10, 2012. The entire contents of these priority applications are incorporated herein by reference.

BACKGROUND OF THE INVENTION

The present invention relates to a stent graft having a hollow cylindrical body with a blood side and a vessel side, wherein the stent graft has a first stent graft portion with a self-expanding stent composed of successive rings of meandering supports in its longitudinal direction, and with a first prosthesis material secured on the rings and connecting these on the vessel side of the hollow cylindrical body.

Stent grafts of this kind are well known in the prior art. These vascular stents, also referred to as intravascular or intraluminal stent grafts, or stents for short, are implanted into blood vessels that have been damaged, for example as a result of diseases or the like, or that have been widened by an aneurysm or have had their lumen occluded, as a consequence of which the function of the vessels is greatly impaired or there is a risk of the vessels rupturing. In the prior art, various implantable stent devices are known which, after they have been implanted, keep blood vessels, for example arteries, open or delimit aneurysms from the blood stream. Such stents generally have a tubular or hollow cylindrical body which is inserted into the vessel and is fixed at the appropriate location in order to keep the lumen of the vessel open.

Thus, the prior art includes stent grafts, for example, which have a wire framework made of a self-expanding material, for example Nitinol, wherein the wire framework can additionally be connected to a tube made of textile or PTFE.

For implantation, the stent or stent graft is radially compressed, such that its cross-sectional surface area can be considerably reduced and it can be easily inserted into the vessel. On account of the resiliency of the metal framework or metal stent, the stent expands back to its original shape and in so doing stretches its jacket surface, which wedges itself internally in the blood vessel.

For implantation, the stents are folded up radially and, with the aid of catheters advanced through the lumen, are then inserted into the blood vessel and placed in the correct position in the vessel. The correct position of the stent can be monitored using X-ray markers, for example. To ensure that the stents remain in the folded-up state during their positioning, they are usually arranged in a sheath or in a sheath-like tube, which presses the stent radially inward and compresses it. This so-called withdrawal tube is pulled back after the stent has been positioned in the vessel, in which process the stent is held axially by an abutment element/slide element, which is also designated as a pusher. The pusher lies in contact with the stent and holds the latter in its axial position, while the withdrawal sleeve also surrounding the pusher is detached from the stent, which is thus able to expand and wedge itself in the blood vessel.

When releasing a self-expanding stent or stent graft, the physician often has to apply a considerable force to the pulling grip of the sleeve tube and to the grip used for positioning the implant and connected to the pusher. Besides the force applied, a further critical point is often that the stent, once released, can no longer be rotated or moved in the vessel in order, if necessary, to position it correctly, since otherwise there is a danger of damaging the vessel.

DE 103 35 948 B3 discloses a stent whose support framework is compressed by a thread that is looped around it. The ends of the thread are diverted from the outside into the support framework and are coupled there.

WO 2011/063972 A1 discloses an insertion system for introducing a medical implant into a vessel of a patient, wherein at least one pulling thread is used with which the diameter of an implant can be changed.

Moreover, US 2007/0100427 A1 describes a device having an intraluminal prosthesis with two thread-like connection elements which enclose the prosthesis in the distal and proximal areas and which can compress the prosthesis by being shortened.

Finally, U.S. Pat. No. 5,776,186 describes an insertion device for stent graft systems that have two Nitinol wire loops which form the framework of the stent graft and via which the stent graft is brought to its expanded shape after the insertion catheter compressing the stent graft has been pulled back.

EP 1 964 532 A2 and EP 1 117 341 B1, for example, disclose an insertion system which permits step-by-step release of a stent/stent graft kept compressed by a sleeve tube. Moreover, in the prior art, so-called pistol grips are known which are intended to allow the physician to gently release a stent graft likewise kept compressed by a sleeve tube.

However, the insertion systems described have the disadvantage that it is impossible or almost impossible with them to position the stent, before it is finally released, i.e. to rotate it and move it, in such a way that it comes to lie correctly. This is critical especially in the case of stents/stent grafts with side branches, since these are of course intended to extend into the branching-off blood vessels after the stent/stent graft has been released.

SUMMARY OF THE INVENTION

Against this background, it is an object of the present invention to make available a stent/stent graft and an alternative release system by means of which the stent/stent graft can be easily compressed, inserted and released in such a way that correct positioning of the stent is possible directly before its final release.

According to the invention, this and other objects are achieved by a development of the stent graft mentioned at the outset, wherein the first stent graft portion thereof has, on at least one of its rings, two loop-shaped fixing elements which are attached via a common fixing area and which are attached to the supports of the rings in such a way that, due to the fact that they are guided in opposite directions around the hollow cylindrical body, the latter is compressible.

The object is further achieved by an insertion system for a stent graft as described above which, in order to compress and insert the stent graft into the blood vessel, moreover has at least one pin element designed to be threaded through and temporarily fix the loop-shaped fixing elements compressing the stent graft.

With the stent graft according to the invention and the insertion system according to the invention, it is possible to correctly position the stent graft and, after it has been positioned, to rotate it, if necessary, in order to position any side branches of the stent graft in branching-off vessels. A step-by-step release of the stent graft is also achieved, with the individual steps of the release being able to be specifically controlled.

With the loop-shaped fixing elements attached to the supports of the stent rings, it is possible to compress the stent graft. The two loop-shaped fixing elements, also designated synonymously as "loops" here and throughout the application, are attached to, preferably sewn onto, the stent rings or supports of the stent graft according to the invention. The loop-shaped fixing elements are attached, preferably sewn on, in a common fixing area on the supports. This common fixing area can extend over a portion of the support or can be punctiform. In order to compress the stent graft, one loop of the two loop-shaped fixing elements is guided around to the right, with respect to the circumference of the stent graft or of the hollow cylindrical body, and one is guided around to the left. The two loops then "meet" at the location lying opposite the fixing points of the fixing elements in the circumference of the hollow cylindrical body, where they can be placed one over the other. In this way, the stent graft can be "tied together" in the area of the fixing elements and thereby compressed.

According to one embodiment of the invention, the loop-shaped fixing elements are made of a thread-like material customarily used in medicine. For example, it is possible to use the same material that is used for securing the stent rings to the prosthesis material. This can be, e.g., a synthetic thread, preferably of polyester, polyamide, polytetrafluoroethylene or ultra-high-molecular-weight polyethylene (UHMPE) or mixtures thereof or has said materials.

In another embodiment of the stent graft according to the invention, the stent graft has two loop-shaped fixing areas attached via a common fixing area or point on each of its rings.

This feature has the advantage that the stent graft can thus be compressed along its entire length.

The loop-shaped fixing elements in the circumference of the hollow cylindrical body of the stent graft can be attached to the supports in a manner offset in relation to one another or adjacent to and behind one another.

According to a further embodiment of the stent graft according to the invention, the first stent graft portion can also have at least one stent side branch, e.g. at least two or three stent side branches, designed to be introduced into a vessel branching off from the blood vessel.

According to a further embodiment, the stent graft has a second stent graft portion with a tubular body composed of a second prosthesis material, which material can be identical to the first prosthesis material or can consist of a different material or have this. The second stent graft portion has no stent rings. Moreover, according to a further embodiment, it may be preferable if this second stent graft portion has at least one stent side branch, more preferably two or three side branches.

The second stent graft portion can be provided in particular for the reconstruction of damaged or injured blood vessels and is generally sewn into such devices in such a way that the areas which are diseased and injured or damaged, or which are no longer functional or are only partly functional, are replaced by the second stent graft portion. For example, the second stent graft portion can in particular be provided for the reconstruction of the aortic arch and of the ascending aorta, especially if this portion has three side branches that are provided respectively for the brachiocephalic trunk, the common carotid artery and the left subclavian artery, into which vessels the side branches are inserted in order to ensure supply of blood to these vessels originating in the aortic arch.

As has been mentioned above, the present invention also relates to an insertion system for inserting a self-expanding stent graft into a blood vessel of a patient, wherein a stent graft as described above is intended to be inserted, wherein the insertion system, in order to compress and insert the stent graft into the blood vessel, moreover has at least one pin element designed to be threaded through and temporarily fix the loop-shaped fixing elements compressing the stent graft, and the pin element has a proximal end and a distal end, and a middle portion lying between the proximal end and distal end.

The pin element provided in the insertion system is thus threaded through the loops which, starting from their fixing location, have each been guided around the stent graft and thereby compress the latter. The threading of the loops means that these are fixed in turn, as a result of which the stent graft remains compressed as a whole. In this compressed form, the stent graft can be inserted into the blood vessel.

Accordingly, upon release, it is thus preferred if the compressed stent graft can be released by pulling the pin element back in the proximal direction and thereby freeing the loops that have kept the stent graft compressed.

Here, "proximal direction" indicates the direction leading toward the user. Moreover, a "pin element" is understood as any elongate, pin-shaped element that is long enough and of such diameter as to be able to be engaged in at least some of the loops provided on the stent graft. Consequently, the pin element has a proximal end and a distal end and a proximal and a distal area, and also, between these two ends or areas, a middle area, wherein the proximal end is closest to the user or the person manipulating the insertion system. The pin elements are preferably made of stainless steel but can be made of any other desired material that is suitable for the present purposes and that has a certain or sufficient stiffness to keep the loops and therefore also the stent graft fixed.

When the pin element is pulled back, the loops are thus released again step by step, as a result of which they are no longer held together at the location in the circumference of the stent lying opposite the fixing location, and the stent is thus no longer compressed and is consequently released.

According to a further embodiment of the insertion system according to the invention, it has several pin elements of different length. These are designed in such a way, and are threaded through the loop-shaped fixing elements for compressing and releasing the stent graft in such a way, that different portions of the stent are releasable by pulling the pin elements of different length back in the proximal direction.

The pin elements are preferably guided with their proximal end through a carrier element and, when the latter is moved in the proximal direction, the pin elements, because of their different length, are carried along one after another in the proximal direction. In this way, stent areas which are fixed/compressed by pin elements of different length can advantageously be released at different times and in a specific way.

If several pin elements of different length are provided in the insertion system according to the invention, it is preferable if the loop-shaped fixing elements are attached to the rings of the stent in a manner offset in relation to one another. In this embodiment, each pin element then engages in a pair of loop-shaped fixing elements. If the loop-shaped fixing elements are attached to the rings in a manner adjacent to one another in the longitudinal direction of the stent graft, it is preferable if one pin element is used. In this case, the one pin element is threaded through all the pairs of loop-shaped fixing elements.

According to a further embodiment, the insertion system according to the invention is additionally provided with a sleeve tube which is arranged over the pin elements compressing the stent in cooperation with the loop-shaped fixing elements.

With this embodiment, it is possible to use both a sleeve tube and also the release mechanism of pin element/loop-shaped fixing elements in order to release the stent graft. This "combined" release mechanism is advantageous particularly in stent grafts that have side branches or arms issuing from the main body of the stent graft. Here, the whole stent graft in general can first of all be released by pulling back the sleeve tube, in which case the stent graft area with the arms still remains compressed by the mechanism composed of pin element and loop-shaped fixing elements. In this way, the side branches/branching-off arms can first of all be positioned correctly, i.e. in the branching-off vessels, before this area is then also released by pulling back the one or more pin elements. In this case, the pin element can also be guided through the arm, i.e. in addition to the passage through the loops.

In another embodiment, provision is also made that the pin element is guided with its proximal end about a roller provided within a handle or housing of the insertion system.

This embodiment has the advantage that, after pulling back the sleeve tube, which is preferably coupled to the handle and is pulled back from the stent graft by pulling the handle in the proximal direction, the release path for the pin elements will still be long enough in order also to guide the pins out of the loops and completely release the stent graft.

It will be appreciated that the insertion system according to the present invention also has any other features customary to stent insertion systems, for example a pusher, catheter tube, etc. Proceeding from the teaching disclosed herein, it will be obvious to a person skilled in the art which further features and properties the insertion system can have in order to be able to function for the particular use. For example, reference is made to EP 1 964 532, the content of which is explicitly incorporated herewith.

Further advantages will become clear from the following description of advantageous embodiments and from the attached figures.

It will be appreciated that the aforementioned features and the features still to be explained below can be used not only in the respectively cited combination but also in other combinations or singly, without departing from the scope of the present invention.

BRIEF DESCRIPTION OF THE DRAWINGS

Illustrative embodiments of the invention are shown in the accompanying figures and are described in more detail below with reference to these figures.

DESCRIPTION OF PREFERRED EMBODIMENTS

Figure 1:
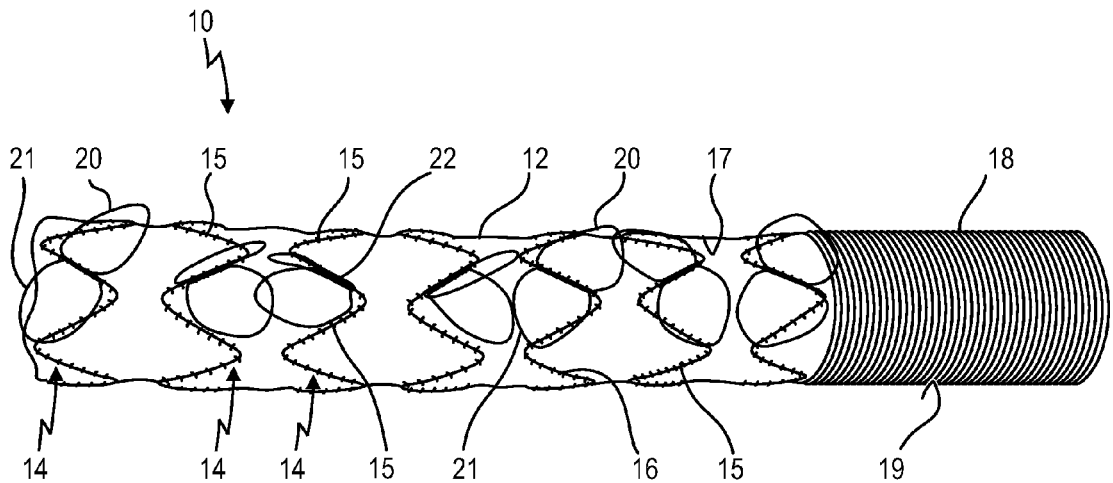
FIG. 1 shows a schematic detail of a first illustrative embodiment of the stent graft according to the invention.

A first embodiment of a stent graft according to the invention, designated generally by reference sign 10 in FIG. 1, has a hollow cylindrical body 11 with a first stent graft portion 12 having a self-expanding stent composed of successive rings 14 of meandering supports (or support elements) 15 in its longitudinal direction. The supports 15 are connected to one another on the outside of the hollow cylindrical body 11 by a prosthesis material 17, which is secured on the supports 15 by stitches 16. The stent graft shown in FIG. 1 also has a second stent graft portion 18. In contrast to the first stent graft portion 12, this second stent graft portion 18 has no stents composed of rings with meandering supports, and instead it merely comprises a second prosthesis material 19.

Moreover, reference signs 20, 21 in FIG. 1 indicate loop-shaped fixing elements or loops, which are situated in pairs on a support 15 of a ring 14 and are attached there on a common fixing area 22. In the example shown in FIG. 1, the loop-shaped fixing elements 20, 21 are sewn onto the supports 15 of a ring 14, specifically via a common portion support 15, which constitutes the fixing area 22. The loops 20, 21 are the same size or approximately the same size.

In the figures, the same features of the various embodiments are provided with the same reference signs. For reasons of clarity, the stitches 16 by which the prosthesis material 17 is connected to the rings 14 of the stent are not shown in FIGS. 2 to 5.

Figure 3:
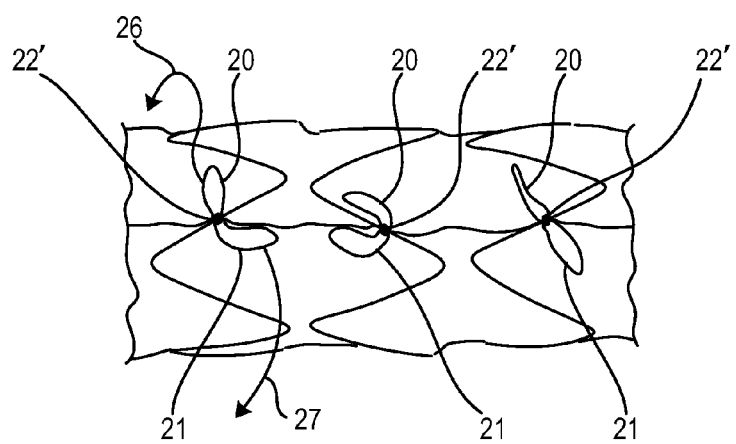
FIG. 3 shows an enlarged detail of a further embodiment of the stent graft according to the invention.

Alternatively, in the embodiment shown in the form of a detail in FIG. 3, the common fixing area 22' of the loop-shaped fixing elements 20, 21 is attached to the supports 15 in a punctiform manner. Moreover, FIG. 3 shows two arrows 26 and 27, which indicate the direction in which the two loop-shaped fixing elements 20, 21 are each guided in order to "bind" or compress the hollow cylindrical body 11 of the stent graft 10.

Figure 2:
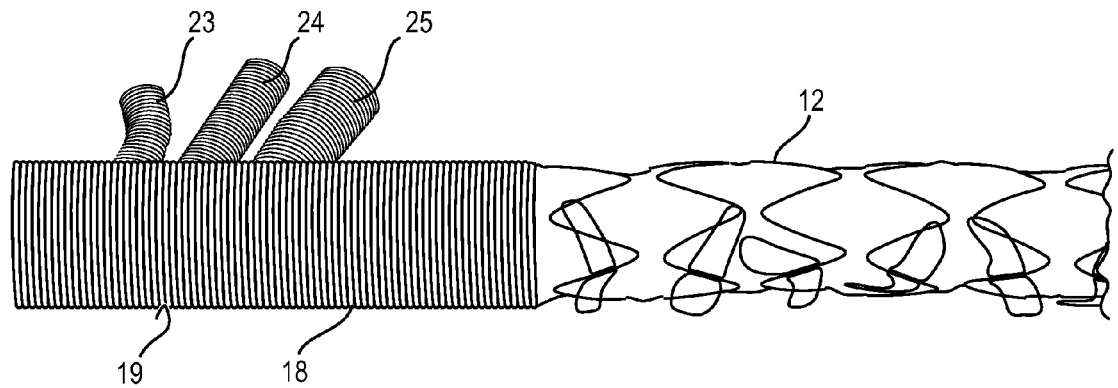
FIG. 2 shows a schematic detail of a further illustrative embodiment of the stent graft according to the invention.

FIG. 2 shows a further embodiment of the stent graft according to the invention. Here, the second stent graft portion 18 has side branches/arms 23, 24, 25, which are provided for introduction into side vessels branching off from the main vessel.

Figure 4:
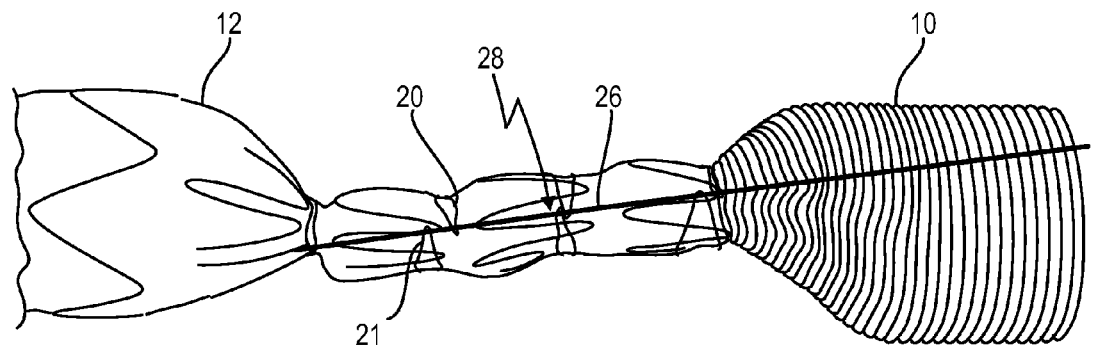
FIG. 4 shows a view in which the illustrative embodiment of the stent graft according to the invention shown in FIG. 1 is in a compressed form with an engaged pin element.

In FIG. 4, the embodiment of the stent graft 10 according to the invention shown in FIG. 1 is shown in a partially compressed state. Here, the loop-shaped fixing elements 20, 21 have each been guided in different circumferential directions around the hollow cylindrical body 11 of the stent graft 12, and then a pin element 26 has been threaded through the loops of the loop-shaped fixing elements 20, 21. As can be seen from FIG. 4, if the loops are each guided in opposite directions around the stent graft, they meet on the areas 28 which lie opposite the fixing areas 22, 22' in the circumference of the stent graft 10, where the pin element 26 is threaded through them.

Figure 5:
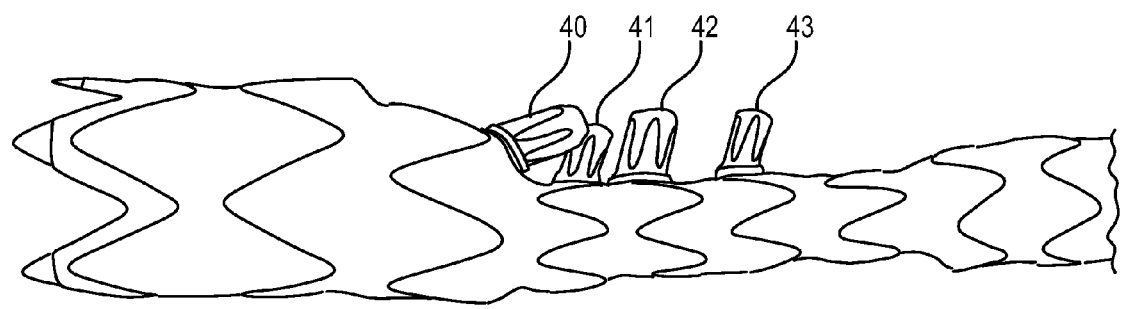
FIG. 5 shows a detail of an embodiment of a stent graft according to the invention.

FIG. 5 shows a further embodiment of the stent graft according to the invention, the first stent graft portion 12 here having arms or side branches 40, 41, 42 and 43, which are provided for side vessels branching off from the main vessel.

The embodiment shown in FIG. 5 can be provided for use, for example, in the abdominal aorta, such that the stent graft 10 is inserted with its hollow cylindrical body 11 into the abdominal aorta in such a way that the side branches 40, 41, 42 and 43 can be placed, for example, in the origins of the celiac trunk, the superior mesenteric artery and both renal arteries. In this embodiment, the pin element 26 can be guided through one of the arms 40, 41, 42, 43 and through the loop-shaped fixing elements 20, 21 compressing the stent graft 10.

Figure 6:
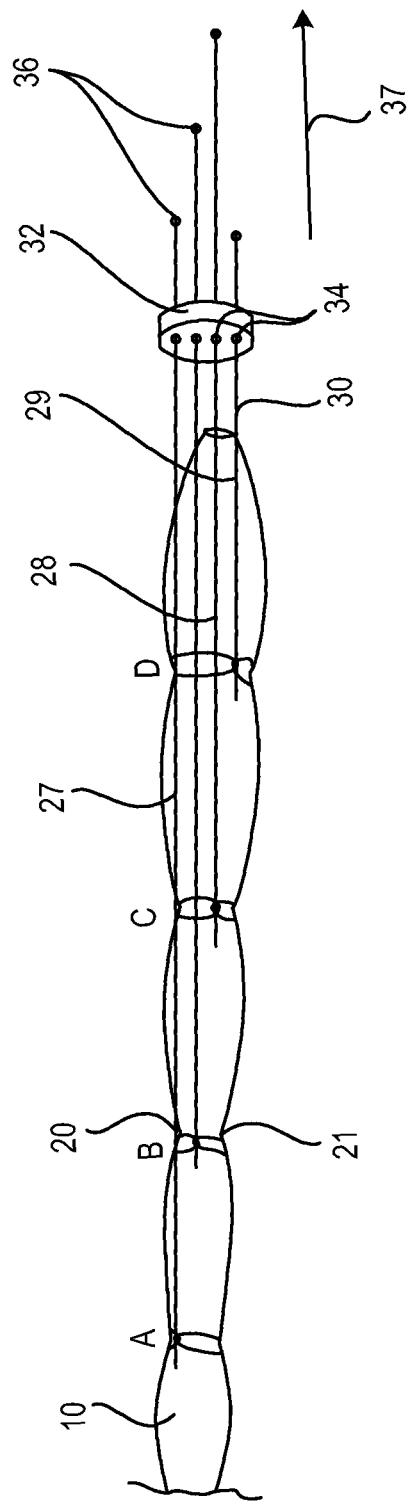
FIG. 6 shows a schematic view of an embodiment of the release system according to the invention for the stent graft according to the invention.

FIG. 6 shows schematically a further embodiment of a release system according to the invention. The embodiment of the stent graft 10 according to the invention as shown in FIG. 6 also has loop-shaped fixing elements 20, 21, which have each been wound in different directions around the stent graft 10. Moreover, several pin elements 27, 28, 29, 30 are provided, which are each threaded through a loop pair 20, 21. Thus, the pin element 27 is threaded through the loop pair 20, 21 designated by A, the pin element 28 is threaded through the loop pair 20, 21 designated by B, the pin element 29 is threaded through the loop pair designated by C, and the pin element 30 is threaded through the loop pair designated by D.

With their proximal end, that is to say the end closer to the user, the pin elements 27, 28, 29 and 30 are guided through a disk-shaped carrier element 32 that has four bores 34 through which the pin elements 27, 28, 29 and 30 are each guided. At the outermost end of the proximal area of the pin elements 27, 28, 29 and 30, there are thickened parts or stop elements 36, of which the diameter is greater than the diameter of the bores 34.

In FIG. 6, arrow 37 indicates the direction in which the pin elements and the carrier element 32 are guided in order to release the stent graft 10 or to release individual stent graft areas in succession. If the carrier element 32 is moved in the proximal direction, i.e. toward the user, it pulls the pin elements 27, 28, 29, 30 with it when it comes into contact with the thickened part or stop element 36, and it specifically does so in the sequence in which the stop elements/thickened parts 36 are taken up by the carrier element 32. Thus, in the example shown in FIG. 6, the pin element 30 is the first to be carried along and pulled in the proximal direction, as a result of which, in the illustrative embodiment shown in FIG. 6, the area D of the stent graft 10 is the first to be released and expanded. As the movement in the proximal direction continues (see arrow 37), the pin element 27 is carried along, such that, after the pin element 27 has been pulled out of the loop pair 20, 21, the area A of the stent graft 10 can expand. Finally, this is followed by areas B and C, which can expand as a result of the sequential carrying of the stop elements 36 of the pin elements 28 and 29 and as a result of these pin elements 28, 29 being unthreaded from the loop pairs 20, 21.

In this way, depending on the arrangement and threading of the pin elements, any desired areas can be deliberately released at different times.

In a further embodiment (not shown), the pin element 26, or the pin elements 27, 28, 29, 30, can be guided and wound up via its or their proximal end(s) on a roller located in a handle or housing for manipulating the release/insertion system. This embodiment is particularly advantageous if, as has been described above, in addition to the release system according to the invention a sleeve tube (not shown in the figures) is also present. This sleeve tube is arranged over the release system according to the invention composed of loop-shaped fixing elements 20, 21 and pin elements 26, 27, 28, 29, 30 and is consequently pulled back from the stent graft 10 before the release system according to the invention. Since the sleeve tube is often coupled to the handle/housing, and the latter is therefore already guided in the proximal direction, there is generally only a short release path for the pin elements 26, 27, 28, 29, 30, which of course then have to be pulled likewise in the proximal direction. By rolling up or winding up the pin elements 26, 27, 28, 29, 30 in the handle, it is ensured that the release path is still long enough to pull the pin elements 26 or 27, 28, 29, 30 out of the loop-shaped fixing elements 20, 21 and thereby release the stent graft 10 in its entirety.

The invention claimed is:

1. A stent graft for inserting into a blood vessel of a patient, having a hollow cylindrical body with a blood side and a vessel side, wherein the stent graft has the following:
 a first stent graft portion with a self-expanding stent composed of successive zig-zag rings of meandering supports in its longitudinal direction, with the zig-zag rings also having a zig-zag form in an expanded state of the stent graft, and with a first prosthesis material secured on the rings and connecting these on the vessel side of the hollow cylindrical body,
 a second stent graft portion with a tubular body composed of a second prosthesis material, wherein the second stent graft portion has no stent rings, and
 wherein, on each of its zig-zag rings, the first stent graft portion has, on each of its rings of meandering supports, two loops which are sewn, respectively, to the meandering supports at only one fixing point, which is shared by the two loops, such that, due to the fact that they are guided in opposite directions around the hollow cylindrical body, the latter is compressible along its entire length, wherein the fixing point is located at the same position for each zig-zag ring.

2. The stent graft as claimed in claim 1, wherein the first stent graft portion moreover has at least one stent side branch designed to be introduced into a vessel branching off from the blood vessel.

3. The stent graft as claimed in claim 1, wherein the second stem graft portion has at least one stent side branch.

4. An insertion system for inserting a self-expanding stent graft into a blood vessel of a patient, wherein the insertion system has
 a stent graft having a hollow cylindrical body with a blood side and a vessel side, wherein the stent graft has a first stent graft portion with a self-expanding stent composed of successive zig-zag rings of meandering supports in its longitudinal direction, with the zig-zag rings also having a zig-zag form in an expanded state of the stent graft, and with a first prosthesis material secured on the zig-zag rings and connecting these on the vessel side of the hollow cylindrical body,
 a second stent graft portion with a tubular body composed of a second prosthesis material, wherein the second stent graft portion has no stent rings, and
 and wherein, on each of its zig-zag rings, the first stent graft portion has, on each of its rings of meandering supports, two loops which are sewn, respectively, to the meandering supports, at only one fixing point, which is shared by the two loops, such, that, due to the fact that they are guided in opposite directions around the hollow cylindrical body, the latter is compressible along its entire length, wherein the fixing point is located at the same position for each zig-zag ring, and in order to compress and insert the stent graft into the blood vessel, the insertion system moreover has at least one pin element designed to be threaded through and temporarily fix the loops compressing the stent graft, wherein the pin element has a proximal end and a distal end, and a middle portion lying between these ends.

5. The insertion system as claimed in claim 4, wherein the compressed stent graft can be released by pulling the at least one pin element back in the proximal direction and thereby freeing the loops that have kept the stent graft compressed.

6. The insertion system as claimed in claim 4, wherein several pin elements of different length are provided for releasing different stent graft portions.

7. The insertion system as claimed in one of claim 4, wherein a sleeve tube is additionally provided which is arranged over the at least one pin elements compressing the stent graft in cooperation with the loops.

8. The insertion system as claimed in claim 4, wherein it moreover has a handle and, within the handle, a roller via which the at least one pin element can be guided with its proximal end.

* * * * *